United States Patent [19]

Wong et al.

[11] Patent Number: 4,838,876

[45] Date of Patent: Jun. 13, 1989

[54] SILICONE RUBBER CATHETER HAVING IMPROVED SURFACE MORPHOLOGY

[75] Inventors: Edward W. Wong, Lexington; Daniel G. Ballan, Holden, both of Mass.

[73] Assignee: The Kendall Company, Boston, Mass.

[21] Appl. No.: 157,171

[22] Filed: Feb. 11, 1988

Related U.S. Application Data

[63] Continuation of Ser. No. 857,262, Apr. 29, 1986, abandoned.

[51] Int. Cl.$^4$ ............................................. A61M 5/325
[52] U.S. Cl. ................................... 604/265; 604/280
[58] Field of Search .................... 604/265, 266, 280; 128/DIG. 21

[56] References Cited

U.S. PATENT DOCUMENTS

| | | | |
|---|---|---|---|
| 3,169,527 | 2/1965 | Sheridan | 604/265 |
| 3,434,869 | 3/1969 | Davidson | 604/266 |
| 3,695,921 | 10/1972 | Shepherd et al. | 604/280 |
| 3,708,324 | 1/1973 | Stebleton | 604/280 |
| 3,962,519 | 6/1976 | Rüsch et al. | 428/409 |
| 4,318,947 | 3/1982 | Joug | 604/280 |
| 4,481,323 | 11/1984 | Sterling | 604/96 |
| 4,534,363 | 8/1985 | Gold | 604/265 |
| 4,686,124 | 8/1987 | Onohara et al. | 604/266 |

Primary Examiner—C. Fred Rosenbaum
Assistant Examiner—Mark F. Colosimo
Attorney, Agent, or Firm—Alvin Isaacs

[57] ABSTRACT

Silicone rubber catheters possessing improved surface morphology, at least the surface of the catheter to be inserted in the body having bonded thereto the reaction product of a composition comprising:

(1) at least one crosslinkable polysiloxane;
(2) an innocuous lubricating agent; and
(3) a crosslinking agent Preferably, the lubricating agent is a medical grade lubricating oil.

15 Claims, No Drawings

SILICONE RUBBER CATHETER HAVING IMPROVED SURFACE MORPHOLOGY

CROSS REFERENCE TO RELATED APPLICATION

This application is a continuation of Applicant's copending application Ser. No. 857,262, filed on Apr. 29, 1986, now abandoned.

BACKGROUND OF THE INVENTION

The present invention is directed to the art of improving the surface morphology of silicone rubber catheters, particularly urethral catheters.

In general, catheters may be described as tubular, flexible, surgical instruments for withdrawing fluids from or introducing fluids into a body cavity. Although catheters are employed for various purposes, the most common usage and the one generally thought of when one mentions catheterization is the catheter introduced into the bladder through the urethra for withdrawal of urine.

While some catheters are employed intermittently, more typically they are indwelling, i.e. retained in the body cavity for extended periods of time. As examples of indwelling catheters, mention may be made of urethral catheters for withdrawal of urine, e.g. Foley catheters, which are retained in the bladder by a balloon which may be inflated with air or liquid; and winged catheters which are provided with two projections at the end inserted in order to retain it in the bladder.

Typically, catheters are made of silicone rubber, latex or some suitable medical grade polymer such as polyvinyl chloride.

Particularly with the use of indwelling catheters such as urethral and venous catheters, it is well recognized that they are often a prime avenue for the introduction of pathogenic organisms. This is perhaps more prevalent with indwelling catheters such as the commonly employed Foley catheter. It is not uncommon for urinary tract infections to be observed within a few days.

Consequently, the patent literature is replete with reference to the art of coating such catheters, e.g. silicone rubber catheters, with various microbiocides, antibiotics or other bioactive reagents in order to ward off infections caused by invading organisms. By way illustration, mention may be made of U.S. Pat. Nos. 4,318,947 issued to Joung; 4,479,795 of Mustacich et. al.; 4,515,593 of Norton; and 4,539,234 of Sakamoto et. al., as well as the patents cited in this patents.

While in its broadest sense, the present invention is also directed to the art of coating catheters to present adverse reactions, particularly infection, induced by their use, the task of invention and, consequently, its solution are vastly different.

While much attention has been focused on coating catheters with a microbiocide or the like in order to bar the avenue for entry of pathogenic organisms, the present invention is instead concerned with an entirely different source of danger, namely infection or other injury which can result from the abrasive nature of the catheter when inserted in the body cavity, specifically those catheters made from silicone rubber.

Of particular concern are urinary tract infections resulting from the use of silicone rubber urethral catheters such as a Foley catheter. While the present invention is not so restricted, it will accordingly be discussed hereinafter, for purposes of illustration, by reference thereto.

In general silicone rubber catheters may be characterized as having a surface which feels somewhat rough and having an undesirably high coefficient of friction. This friction can induce abrasion to the delicate cavity walls, e.g. mucosa or endothelia linings, into which it is inserted and the abrasive action can in turn provide a source of infection.

The task of the invention may accordingly be said to improve the surface morphology so as to provide a smooth, lubricious surface which will appreciably lower the coefficient of friction and greatly facilitate insertion minimizing if not totally preventing harmful abrasion.

BRIEF DESCRIPTION OF THE INVENTION

In accordance with the present invention, the aforementioned task is solved by applying to the surface of the catheter from a liquid vehicle at least one crosslinkable polysiloxane, an innocuous, medical grade lubricating agent, and a crosslinking agent; and thereafter heating the thus coated catheter to remove the solvent and to initiate crosslinking, thereby bonding the coated composition to the surface of the silicone rubber catheter.

DETAILED DESCRIPTION OF THE INVENTION

As previously mentioned, the present invention is directed to the task of improving the surface morphology of silicone rubber catheters to provide a smooth surface which has a lower coefficient of friction and may thus be inserted in the body cavity without causing abrasion and the problems resulting therefrom.

The invention is particularly directed to silicone rubber urethral catheters, e.g. those per se known in the art, where the abrasive action resulting from insertion of these indwelling catheters may cause urinary tract infections. However, it will be appreciated by those skilled in the art that the invention is equally applicable to any catheters, whether indwelling or of the intermittent variety, where abrasion can be a source of concern. For example, it is envisioned that the abrasive force of a catheter inserted into the circulatory system, e.g. a cardiac or central venous catheter, may damage the endothelial lining of the vessel and may accordingly be a potential source of blood clotting.

In accordance with invention, the surface morphology of silicone rubber catheters is substantially improved by bonding to the surface of at least that portion to be inserted in a body cavity, a coating comprising the reaction product of a composition comprising:

(1) at least one crosslinkable polysiloxane; (2) an innocuous medical grade lubricating oil; and (3) a crosslinking catalyst.

The coating may be applied to the silicone rubber surface from a liquid vehicle, preferably a volatile organic solvent, followed by heating to drive off the organic solvent or other liquid vehicle and to effect crosslinking. The manner of application, whether by dipping, flowing, spraying, etc. is a matter of individual choice and per se comprises no part of this invention.

As used herein, the term "crosslinkable" refers to a polysiloxane having reactive or functional groups which may be crosslinked. Silicone polymers of this description are generally known and commercially available. By way of illustration, mention may be made of dimethyl polysiloxane, methylphenyl polysiloxane, cyanoalkylmethyl polysiloxane, and fluoroalkylmethyl siloxane. A particularly preferred crosslinkable polysiloxane is dimethyl polysiloxane which is characterized as possessing high strength and elasticity.

As used herein with respect to the lubricating oil, the term "innocuous" means that the oil will not adversely react with the polysiloxane, e.g. preclude its ability to crosslink and thereby bond to the surface of the catheter. It will be appreciated that the lubricating oil must also be medical grade for its intended use of insertion into a body cavity. It will also be appreciated that the lubricating oil should also be compatible with the polysiloxane. Lubricating oils of this description will be readily apparent to those skilled in the art and also per se comprises no part of this invention.

The preferred lubricating agents are those within the class know in the art as medical fluids, the most preferred being silicone oils, e.g. DC-360 (trade designation of Dow Corning.)

In addition to the crosslinking catalyst, the coating composition will preferably also contain a crosslinking accelerator. While in theory, any silicone crosslinking agent and accelerator may be employed, applicants have determined that a low temperature fast cure paper release coating formulation commercially available from Silicone Products Department, General Electric Company is ideally suited. This formulation consists of a crosslinkable polysiloxane (sold under product designation: SS4191): a crosslinking catalyst (SS4192C); and an accelerator (SS4259C).

The crosslinkable polysiloxane, SS4191, is understood in fact to be a blend of about 94% polydimethylsiloxane with about 6% methyl, hydrogen polysiloxane.

The catalyst for the system, SS4192C is dibutyltin diacetate $[(C_4H_9)_2Sn(OCOCH_3)_2]$.

The accelerator, 554259C, is a polysiloxane having pendant amino groups.

The ratios or amounts of reagents in the coating composition will vary and will be apparent to those skilled in the art.

In general, the ratios (solids content) of crosslinkable polysiloxane to lubricating oil will be on the order of about 8:1 to about 3:1.

The levels of catalyst and accelerator are readily determined by starting with given levels and ascertaining whether the cure is complete or incomplete. Obviously, no more of the curatives than are necessary should be employed. On the other hand, when the cure is incomplete, the levels can be then be increased in slow increments until the cure is complete.

While the levels will vary in accordance with the particular reactants employed, with the particular G.E. formulation described above, optimum results were found using levels (dry weight) of 100 parts of the crosslinkable polysiloxane and about 6.5 parts for each of the catalyst and accelerator.

The solvent for the coating solution is not critical and will be readily suggested to the skilled worker. Preferably, low boiling organic solvents are employed. Useful solvents include the Freons, i.e. halogenated hydrocarbons such as 1,1,2-trichlorotrifluormethane; heptane, etc.

The coating composition of this invention is readily prepared by mixing the ingredients under ambient temperature and pressure. The catheter may be coated by per se known techniques, dipping in the coating solution being more efficacious.

Crosslinking as well as solvent removal is effected by heating at a temperature and for a time to effect complete cure as well as solvent removal. Since there is a time—temperature relationship to effect cure, the time and temperature are not susceptible to precise quantitative statements. As will be seen from the following illustrative example, on a laboratory level, heating at about 350° F. (150° C.) for about one minute is effective. However, with production equipment employing higher temperature a shorter time will be required.

The following example shows by way of illustration and not by way of limitation the practice of this invention.

EXAMPLE 2.56 g of a 30% solution of SS4191 curable dimethyl polysiloxane in toluene, 0.2 g of DC-360 medical fluid (1000 cps), 0.1 g of a 50% solution of SS4259C accelerator in toluene, and 0.1 g of a 50% solution of SS4192C catalyst in toluene were added with rapid stirring up 147.0 g of heptane to yield approximately 150 g (total weight) of coating solution. To insure complete coating, a Foley silicone rubber catheter was dipped twice into the resulting solution and then flash dried in an oven at 350° F. (150° C.) for about one minute. While not measure, the coating was calculated to be less then one mil thick.

The coating bonded firmly to the catheter surface and resisted separation and scratching. It was smooth and slightly lubricious to the touch.

To evaluate its thermal stability, the coated catheter was annealed at 350° F. for sixteen hours. Gross exam revealed no appreciable change in the lubricity of the coating. This was also confirmed by drag reduction tests on a standard (model SP-101) slip/peel tester.

A catheter coated as described above (test) was compared with an identical uncoated one (control) on the SP-101 slip/peel tester. The catheter was placed on a platter between stainless steel/stainless steel surfaces with a static weight load on top. For comparative evaluation, the thickness of the platter and weight remained constant. The load cell was connected to the catheter tube using a metal hook through the drain hole. The following control was used:

| TIME SELECTOR | 10 SECONDS |
| --- | --- |
| METER SELECT SWITCH | AVERAGE |
| PLATTER SPEED | 12 IN/MIN |
| LOAD WEIGHT | 200 G SLED WEIGHT |

The test was repeated substituting glass/glass surfaces for the steel/steel. The coefficient of friction (COF) for the test and control in each of the above tests were determined. For the stainless steel/stainless steel test, the uncoated showed and average COF of 0.128, while the coated had an average of 0.098 (a ratio of 0.76 or 23% reduction). For the glass/glass test, the control showed an average COF of 0.204, and the control 0.107 (a ratio of 0.52 or a reduction on COF of 47%). While the measurement of COF by this method are not considered to be absolute, depending greatly on control conditions, they nevertheless unequivocally demonstrate a dramatic drag reduction.

The foregoing experimentations establish that the silicone coating is thermally stable and will provide very significant reduction in drag, e.g. as much as 50%. While obviously not a prime object of this invention, it should nevertheless be noted that subjective visual observations demonstrate that the coated catheters of this invention is more attractive and aesthetically pleasing to the eye.

From a manufacturing standpoint, the coated catheter is inexpensive and easy to produce in mass quantities.

In use, the silicone-treated Foley catheter of this invention is found to be pliable and less irritating to the urethra and bladder than catheters made of latex or coated latex. Its slick surface and inert nature help to reduce substantially the usual buildup of encrusting urinary salts in drainage lumen. Because there is less clogging encrustation, there is better drainage. The need for frequent catheter changes is also greatly reduced.

While for aesthetic purposes it is desirable that the entire length of the catheter tube be coated for uniformity of appearance, from a functional standpoint, it will be appreciated that only the portion to be inserted need be so coated.

While the invention is primarily directed to urethral catheters, as previously stated the invention is not so restricted and is in fact applicable to both indwelling and intermittent catheters such as those heretofore employed.

Since certain changes may be made without departing from the scope of the invention herein described, it is intended that all matter contained in the foregoing description, including the examples shall be taken as illustrative and not in a limiting sense.

We claim:

1. A silicone rubber catheter having improved surface morphology, said catheter having a portion thereof adapted for insertion in the body, at least the said portion of said catheter having chemically bonded through crosslinking to the surface thereof a smooth continuous outer layer comprising a crosslinked polysiloxane, said outer layer further including an innocuous lubricating agent.

2. A catheter as defined in claim 1 wherein said lubricating agent is an oil.

3. A catheter as defined in claim 2 wherein said oil is a medical grade silicone oil.

4. A catheter as defined in claim 1 wherein said chemically bonded outer layer is provided by effectively crosslinking a composition comprising a crosslinkable polysiloxane, and innocuous medical grade lubricating oil and a crosslinking catalyst.

5. A catheter as defined in claim 4 where in said polysiloxane comprises dimethyl polysiloxane.

6. A catheter as defined in claim 4 wherein said lubricating oil is a silicone oil.

7. A catheter as defined in claim 1, wherein said catheter is a Foley catheter.

8. A Foley silicone rubber urethal catheter having improved surface morphology, said Foley catheter having a portion thereof adapted for insertion into the urethal, at least the said portion of said Foley catheter having been chemically bonded through crosslinking to the surface thereof to constitute a smooth continuous lubricious outer layer comprising a crosslinkable poly siloxane.

9. A process of improving the surface morphology of a silicone rubber catheter having a portion thereof adapted for insertion in the body, comprising the steps of applying to the surface of at least the said portion a composition comprising a crosslinkable polysiloxane, a lubricating agent and a crosslinking agent in a liquid vehicle; and thereafter heating said portion at a temperature and for a time sufficient to remove said liquid vehicle and to chemically bond through crosslinking to the surface of said portion the crosslinkable polysiloxane, thereby providing an improved catheter surface which is a smooth, continuous outer layer.

10. A process as defined i claim 9 wherein said liquid vehicle is a volatile organic solvent for said composition.

11. A process as defined in claim 10 wherein said lubricating agent is an oil.

12. A process as defined in claim 11 wherein said oil is a medical grade silicone oil.

13. A process as defined in claim 12 wherein said catheter is indwelling.

14. A process as defined in claim 12 wherein said catheter is a urethral catheter.

15. A process as defined in claim 12 wherein said catheter is a Foley Catheter.

* * * * *